United States Patent [19]
John et al.

[11] Patent Number: 4,528,027
[45] Date of Patent: Jul. 9, 1985

[54] ACYLTHIO-SUBSTITUTED TRIAZINES

[75] Inventors: William W. John; Kurt H. Pilgram, both of Modesto; Mae E. F. Martin, Manteca, all of Calif.

[73] Assignee: Shell Oil Company, Houston, Tex.

[21] Appl. No.: 613,495

[22] Filed: May 24, 1984

[51] Int. Cl.³ ................ C07D 251/50; C07D 251/52; A01N 43/70
[52] U.S. Cl. ........................................ 71/93; 544/210; 544/206; 544/205; 544/208
[58] Field of Search ................... 71/93; 544/210, 206, 544/205, 208

[56] References Cited

U.S. PATENT DOCUMENTS 3,743,643  7/1973  Brown et al. ...................... 544/210
4,007,032  2/1977  Berrer ................................ 544/210

Primary Examiner—John M. Ford

[57] ABSTRACT

Certain tri-substituted s-triazines, in which one substituent is an acylthioamino moiety, and their use for controlling growth of plants.

3 Claims, No Drawings

ACYLTHIO-SUBSTITUTED TRIAZINES

BACKGROUND OF THE INVENTION s-Triazines of the formula

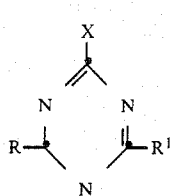

wherein X represents halogen, lower alkoxy or lower alkylthio, and each of R and R¹ represents one of certain substituted-amino moieties, make up a well-known class of herbicides.

For convenience in handling and effectiveness of application, liquid formulations of herbicides often are to be preferred. To minimize formulation, handling, shipping and storage costs, it is general practice to formulate the active compound as a concentrate, which is diluted with water just before application. Solutions of the compounds are most convenient. However, many such compounds are not sufficiently soluble in water to enable aqueous concentrates—indeed, many such compounds are not sufficiently soluble in water to enable their application as dilute solutions. Therefore, such a water-insoluble compound is commonly formulated as an emulsible concentrate, in which the compound is in solution in an organic solvent that is physically and economically suitable—xylene is an example—which also contains one or more surface-active agents. Just prior to application, the concentrate is mixed with water, whereupon on emulsion forms, with very small droplets of the solution of compound being suspended in the water. To enable the use of an emulsible concentrate of the compound, the compound must have substantial solubility in the organic solvent. The triazines above are only slightly soluble in such solvents, so that formulation of such a triazine as emulsible concentrate ordinarily is not feasible.

DESCRIPTION OF THE INVENTION

It has now been found that certain derivatives of such triazines retain essentially the levels and spectra of activity of the parent triazines, but are substantially more soluble in solvents suitable for use in emulsible concentrate formulations, thus being more adapted to formulation in such a mode.

These new derivatives are described by the formula

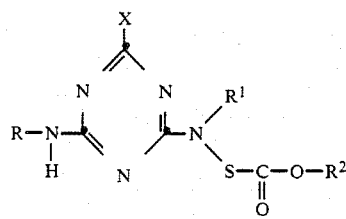

wherein X is middle halogen, alkoxy or alkylthio of one to three carbon atoms, R is alkyl of two to four carbon atoms, cycloalkyl of three to four carbon atoms, or 1-cyanoalkyl of three to five carbon atoms; R¹ is alkyl of one to four carbon atoms or cyclopropyl; R² is alkyl of from one to eight carbon atoms.

By "middle halogen" is meant chlorine and bromine. Each alkyl moiety suitably is either straight-chain or branched-chain in configuration.

Of most interest, because of their activity with respect to plants, are the compounds of the subclass of Formula I wherein X is chlorine, methoxy or methylthio; R is 1-cyano-1-methylethyl, ethyl, isopropyl or cyclopropyl; R¹ is ethyl, isopropyl or cyclopropyl and R² is alkyl of one to four carbon atoms.

Compounds of formula I can be prepared by treating the appropriate triazine of the formula

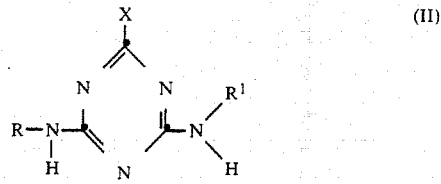

with the appropriate R²-oxycarbonylsulfenyl chloride

in the presence of an inert solvent and in the presence of a nitrogen base as hydrogen halide acceptor.

Treatment of the triazine with the sulfenyl halide is conveniently conducted by adding the halide to a stirred solution of the triazine in a solvent at a temperature of about 0°–20° C., slowly adding an amine thereto, then stirring the reaction mixture at room temperature until the reaction is complete. Suitable solvents are haloalkanes or aromatic hydrocarbons. A preferred nitrogen base is N,N-diisopropylethylamine. Conduct of the treatment in particular instances, and illustration of the workup of the reaction mixtures, and isolation of the products, effected by conventional techniques, are illustrated in the examples hereafter.

The triazine precursors (of Formula II) are known compounds, they and methods for their preparation being disclosed in such patents as U.S. Pat. Nos. 3,505,325, 2,891,855, and 3,766,182 and German Offenlegungschrift Nos. 2,045,601, 2,104,232 and 2,126,640.

The sulfenyl halides of Formula III and methods for their preparation are known: G. Zumach and E. Kuhle, Angewandte Chemie, International Edition, 9, 54–63 (1970); H. Bohme and M. Clement, Liebig's Annalen der Chemie, 576, 61–69 (1951); H. Bohme and H. D. Steudel, Liebig's Annalen der Chemie, 730, 121–132 (1969).

The preparation, isolation and physical properties of typical individual species of the compounds of Formula I, in particular instances, are described in the following examples. In each case, the identity of the product, and each of any intermediate involved, was confirmed by appropriate chemical and spectral analyses.

EXAMPLE 1

2-chloro-4-(1-cyano-1-methylethylamino)-6-(N-ethyl-N-((methoxycarbonyl)thio))-1,3,5-triazine (1)

19.8 g of anhydrous methanol was added drop-by-drop to stirred 81.3 g of (chlorothio)formyl chloride at 30°–60° C. The mixture was stirred for 20 minutes at room temperature, then distilled at 95 Torr. pressure in a Vigreaux column to give (methoxycarbonyl)sulfenyl chloride, (1A) as a fraction boiling at 75°–79° C. (pot), 60°–72° C. (head). 7.5 g of 1A was added to a stirred solution of 10.0 g of 2-chloro-4-(1-cyano-1-methylethylamino)-6-ethylamino-1,3,5-triazine (1B; cyanazine) in 200 ml of methylene chloride at 0°–5° C. Then, at that temperature 7.6 g of N,N-diisopropylethylamine was added drop-by-drop to the stirred mixture. Then the mixture was stirred at room temperature for 14 hours, poured over 200 ml of ice water, and made acidic with hydrochloric acid. The phases were separated. The organic phase was washed with water and dried (MgSO$_4$), and the solvent was evaporated. The residue was chromatographed twice over a column of silica gel, using a 2:15:33 v:v:v mixture of tetrahydrofuran, ethyl acetate and hexane as eluent. Two fractions were obtained, 1 being the second fraction with Rf=0.27, an amber oil, boiling point not determined.

EXAMPLE 2

2-chloro-4-(1-cyano-1-methylethylamino)-6-(N-ethyl-N-((ethoxycarbonyl)thio))-1,3,5-triazine (2)

2 was prepared, as an orange syrup, boiling point not determined, by treating 1B with (ethoxycarbonyl)sulfenyl chloride (2A) according to the procedures described in Example 1. 2A was prepared by the procedure described in Example 1 for the preparation of 1A, from ethanol, rather than methanol.

EXAMPLE 3

2-chloro-4-(1-cyano-1-methylethylamino)-6-(N-ethyl-N-((1-methylpropoxy)carbonyl)thio))-1,3,5-triazine (3)

94.5 g of potassium was added in portions to 1500 ml of 2-butanol under nitrogen, the temperature of the mixture being allowed to rise from room temperature to 85° C. The resulting solution was cooled to 15° C. and 162 g of carbonyl sulfide was added, with stirring. The resulting mixture was stirred at room temperature for 2 hours, diluted with one liter of ether and filtered. The solid thus obtained was washed with ether and dried to give the potassium salt of the 0-(1-methylpropyl)ester of thiocarbonic acid (3A), as an off-white solid, m.p.: 230°–240° C. (with decomposition).

188.4 g of acetyl chloride was added drop-by-drop over a 2-hour period to a stirred suspension of 395 g of 3A in 1500 ml of methylene dichloride at −15° C. The resulting mixture was stirred at −15° C. to −5° C. for 2 hours, at 0° C. for 3 hours and at room temperature for 18 hours. The mixture was filtered and the filtrate was concentrated at about 30 Torr. and 30° C., to give thiocarbonic acid, anhydrosulfide with thioacetic acid, O-(1-methylpropyl)ester (3B), as a pale yellow oil.

A solution of 188 g of chlorine in 3 liters of cold methylene chloride was added drop-by-drop (2.5 hours) to a mixture of 372 g of 3B and 1 liter of methylene chloride at −20° C. to 10° C. The resulting mixture was held at room temperature for 18 hours. The mixture was concentrated at 30 Torr. and 25° C. The residue was vacuum distilled to give ((1-methylpropoxy)carbonyl)-sulfenyl chloride (3C), as a fraction (light yellow) collected at 45°–50° C., 5 Torr.

3 was prepared, as an amber syrup, boiling point not determined, by treating 1B with 3C, according to the procedures described for preparing 1 from 1A and 1B, Example 1.

EXAMPLE 4

2-chloro-4-(1-cyano-1-methylethylamino)-6-(N-ethyl-N-((1,1-dimethylethoxy)carbonyl)thio)-1,3,5-triazine 4)

((1,1-dimethylethoxy)carbonyl)sulfenyl chloride (4A) was prepared, as a yellow liquid, b.p.: 44°–46° C. (1.5 Torr.) from tert-butyl alcohol according to the procedures described in Example 3 for preparing 3C. Treatment of 1B with 4A, according to the procedures described in Example 1 for preparing 1 from 1A and 1B, gave 4, as an amber syrup, boiling point not determined.

EXAMPLES 5–8

2-chloro-4-(1-methylethylamino)-6-(N-ethyl-N-((methoxycarbonyl)thio)-1,3,5-triazine (5)
2-chloro-4-(1-methylethylamino)-6-(N-ethyl-N-(ethoxycarbonyl)thio)-1,3,5-triazine (6)
2-chloro-4-(1-methylethylamino)-6-(N-ethyl-N-((1-methylpropoxy)carbonyl)thio)-1,3,5-triazine (7)
2-chloro-4-(1-methylethylamino)-6-(N-ethyl-N-((1,1-dimethylethoxy)carbonyl)thio)-1,3,5-triazine (8)

5, 6, 7 and 8 were prepared, as an amber liquid, an amber syrup, a yellow syrup, and a yellow syrup, respectively (boiling points not determined) by treating 2-chloro-4-ethylamino-6-(1-methylethyl)amino-1,3,5-triazine (atrazine; commercial) with 1A, 2A, 3C and 4A, respectively, according to the procedures described in Example 1 for preparing 1 from 1A and 1B.

EXAMPLE 9

2-chloro-4-(1-methylethylamino)-6-(N-cyclopropyl-N--((1-methylpropoxy)carbonyl)thio)-1,3,5-triazine (9)

A mixture of 28.5 g of cyclopropylamine and 50.5 g of triethylamine was added drop-by-drop to a stirred solution of 92.3 g of cyanuric chloride in 1.5 liters of dry acetone at room temperature. Then the acetone was evaporated and the residue was treated with a 1:1 v:v mixture of ice water and ether. The ether phase was separated and dried (MgSO$_4$), and the ether was evaporated to give 2-cyclopropyl-4,6-dichloro-1,3,5-triazine (9A), as a white solid, m.p.: 106°–107° C.

A mixture of 9.5 g of isopropylamine and 16.2 g of triethylamine was added drop-by-drop to a stirred solution of 33 g of 9A in 500 ml of dry acetone at room temperature. The reaction was monitored by thin layer chromatography and further isopropylamine was added until only one product was shown. The solvent was evaporated, and the residue was treated with a 1:1 v:v mixture of ice water and ether. The ether phase was separated and dried (MgSO$_4$), and the solvent was evaporated to give 2-chloro-4-(cyclopropylamino)-6-(1-methylethylamino)-1,3,5-triazine (9B), as a white solid, m.p.: 160.5°–161° C.

9 was prepared, as an amber syrup, boiling point not determined, by treating 9B with 3C, according to the procedures described in Example 1 for preparing 1 from 1A and 1B.

EXAMPLE 10

2-chloro-4-(1-methylethylamino)-6-(N-(cyclopropylamino)-N-((1-methylheptyloxy)carbonyl)thio)-1,3,5-triazine (10)

10 was prepared, as an amber syrup, by the procedures described in Example 1 for preparing 1, employing 2-octanol instead of methanol, and 9B, instead of 1B.

EXAMPLES 11 AND 12

2-chloro-4-ethylamino-6-(N-ethyl-N-((methoxycarbonyl)thio)-1,3,5-triazine (11)
2-chloro-4-ethylamino-6-(N-ethyl-N-((1-methylpropoxy)carbonyl)thio)-1,3,5-triazine (12)

11 and 12 were prepared, as off-white solids, m.p.: 95°–97° C., and 80°–83° C., respectively, by treating commercial simazine (est. 98.5% w 2-chloro-4,6-bis(ethylamino)-1,3,5-triazine) with 1A and 3C, respectively, according to the procedures described in Example 1 for the preparation of 1 from 1A and 1B, and Example 3 for the preparation of 3 from 1B and 3C.

EXAMPLE 13

2-methoxy-4-(1-methylethylamino)-6-(N-cyclopropyl-N-((methoxycarbonyl)thio))-1,3,5-triazine (13)

2.1 g of sodium was added in portions to 400 ml of stirred anhydrous methanol. The solution was allowed to cool to room temperature, then 16.5 g of 9B was added and the mixture was refluxed for 2 hours. The solvent was evaporated, and the residue was washed with water, then extracted with ether. The extract phase was dried ($MgSO_4$) and stripped of solvent to give 2-methoxy-4-(cyclopropylamino)-6-(1-methylethylamino)-1,3,5-triazine (13A).

13 was prepared, as an off-white solid, m.p.: 77°–80° C., by treating 13A with 1A as described for preparing 1 from 1A and 1B, Example 1.

EXAMPLE 14

2-methoxy-4-(1-methylethylamino)-6-(N-ethyl-N-((methoxycarbonyl)thio))-1,3,5-triazine (14)

2-methoxy-4-(1-methylethylamino)-6-ethylamino-1,3,5-triazine (14A) (Atraton) was prepared as a white solid (recrystallized from hexane), m.p.: 95°–96° C., by treating atrazine (Examples 5–8) with sodium methoxide according to the procedure described for preparing 13A from 9B, Example 13.

14 was prepared, as an amber syrup, boiling point not determined, by treating 14A with 1A as described for preparing 1 from 1A and 1B, Example 1.

EXAMPLE 15

2-(methylthio)-4-(1-methylethylamino)-6-(N-ethyl-N-((methoxycarbonyl)thio))-1,3,5-triazine (15)

1 g of sodium was added to 100 ml of dry methanol. The solution was allowed to cool to room temperature, 12 g of methanethiol was added, then 4.5 g atrazine, and the mixture was refluxed for 2 hours. The solvent was evaporated, the residue was dissolved in water, and the solution was extracted with ether. The extract phase was dried ($MgSO_4$) and the solvent was evaporated. The residue was dissolved in a minimum amount of boiling hexane. The solution was cooled and the solid product was collected and dried to give 2-(methylthio)-4-(1-methylethylamino)-6-(ethylamino)-1,3,5-triazine (15A) (Ametryne).

15 was prepared as an amber syrup, boiling point not determined, by treating 15A with 1A, according to the procedure described in Example 1 for preparing 1 from 1A and 1B.

Compounds of Formula I have been found to adversely affect the growth of plants, many of which are commonly considered as weeds, and therefore to be useful for controlling the growth of such unwanted plants. Compounds of Formula I have been found to have selectivity with respect to some crop plants—i.e., they control weeds at dosages at which they do not significantly harm the crop plants. Compounds of Formula I appear to be effective when applied preemergence or preplant incorporated (applied to the soil before the seeds have sprouted) or when applied postemergence (applied to the foliage of the growing plant).

Accordingly, the invention includes a method of combatting unwanted plants which comprises applying to the locus an effective amount of a compound of Formula I. In cases where it is desired to control weeds in crop plantings, it is of course preferable to employ the lowest dosage that will control the weeds, for this will minimize any possible deleterious effect of the compound upon the crop plants.

For application, the compound of Formula I ordinarily is applied most effectively by formulating it with a suitable inert carrier or surface-active agent, or both. The invention, therefore, also includes compositions suitable for combatting unwanted plants, such compositions comprising an inert carrier or surface-active agent, or both, and as active ingredient at least one compound of Formula I.

The term "carrier" as used herein means an inert solid or liquid material, which may be inorganic or organic and of synthetic or natural origin, with which the active compound is mixed or formulated to facilitate its application to the plant, seed, soil or other object to be treated, or its storage, transport and/or handling. Any of the materials customarily employed in formulating pesticides, herbicides, or fungicides, are suitable.

Suitable solid carriers are natural and synthetic clays and silicates, for example, natural silicas such as diatomaceous earths; magnesium silicates, for example, talcs; magnesium aluminum silicates, for example, attapulgites and vermiculites; aluminum silicates, for example, kaolinites, montmorillonites and micas; calcium carbonate; calcium sulfate; synthetic hydrated silicon oxides and synthetic calcium or aluminum silicates; elements such as, for example, carbon and sulfur; natural and synthetic resins such as, for example, coumarone resins, polyvinyl chloride and styrene polymers and copolymers; bitumen; waxes such as, for example, beeswax, paraffin wax, and chlorinated mineral waxes; solid fertilizers, for example, superphosphates; and ground, naturally-occurring, fibrous materials, such as ground corncobs.

Examples of suitable liquid carriers are water, alcohols such as isopropyl alcohol and glycols; ketones such as acetone, methyl ethyl ketone, methyl isobutyl ketone and cyclohexanone; ethers such as cellosolves; aromatic hydrocarbons such as benzene, toluene and xylene; petroleum fractions such as kerosene, light mineral oils; chlorinated hydrocarbons such as carbon tetrachloride, perchloroethylene and trichloromethane. Also suitable are liquefied, normally vaporous and gaseous compounds. Mixtures of different liquids are often suitable.

The surface-active agent may be an emulsifying agent or a dispersing agent or a wetting agent; it may be non-ionic or ionic. Any of the surface-active agents usually applied in formulating herbicides or insecticides may be used. Examples of suitable surface-active agents are the sodium and calcium salts of polyacrylic acids and lignin sulfonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; condensates of these with ethylene oxide and/or propylene oxide; condensation products of fatty alcohols or alkyl phenols, for example, p-octylphenol or p-octylcresol, with ethylene oxide and/or propylene oxide; sulfates or sulfonates of these condensation products, alkali or alkaline earth metal salts, preferably sodium salts, of sulfuric or sulfonic acid esters containing at least 10 carbon atoms in the molecule, for example, sodium lauryl sulfate, sodium secondary alkyl sulfates, sodium salts of sulfonated castor oil, and sodium alkylaryl sulfonates such as sodium dodecylbenzene sulfonate; and polymers of ethylene oxide and copolymers of ethylene oxide and propylene oxides.

The compositions of the invention may be prepared as wettable powders, dusts, granules, solutions, emulsifiable concentrates, emulsions, suspension concentrates and aerosols. Wettable powders are usually compounded to contain 25 to 75% by weight of active compound and usually contain, in addition to the solid carrier, 3–10% by weight of a dispersing agent, 2–15% of a surface-active agent and, where necessary, 0–10% by weight of stabilizer(s) and/or other additives such as penetrants or stickers. Dusts are usually formulated as a dust concentrate having a similar composition to that of a wettable powder but without a dispersant or surface-active agent, and are diluted in the field with further solid carrier to give a composition usually containing 0.5–10% by weight of the active compound. Granules are usually prepared to have a size between 10 and 100 BS mesh (1.676–0.152 mm), and may be manufactured by agglomeration or impregnation techniques. Generally, granules will contain 0.5–25% by weight of the active compound, 0–1% by weight of additives such as stabilizers, slow release modifiers and binding agents. Emulsifiable concentrates usually contain, in addition to the solvent and, when necessary, cosolvent, 10–50% weight per volume of the active compound, 2–20% weight per volume emulsifiers and 0–20% weight per volume of appropriate additives such as stabilizers, penetrants and corrosion inhibitors. Suspension concentrates are compounded so as to obtain a stable, non-sedimenting, flowable product and usually contain 10–75% weight of the active compound, 0.5–5% weight of dispersing agents, 1–5% of surface-active agent, 0.1–10% weight of suspending agents, such as defoamers, corrosion inhibitors, stabilizers, penetrants and stickers, and as carrier, water or an organic liquid in which the active compound is substantially insoluble; certain organic solids or inorganic salts may be dissolved in the carrier to assist in preventing sedimentation or as antifreeze agents for water.

Of particular interest in current practice are water-dispersible granular formulations. These are in the form of dry, hard granules that are essentially dust-free, and are resistant to attrition on handling, thus minimizing the formation of dust. On contact with water, the granules readily disintegrate to form stable suspensions of the particles of active material. Such formulations contain 90% or (up to 95%) more by weight of finely divided active material, 3–7% by weight of a blend of surfactants, which act wetting, dispersing, suspending and binding agents, and may contain up to 3% by weight of a finely divided carrier, which acts as a resuspending agent.

Aqueous dispersions and emulsions, for example, compositions obtained by diluting a wettable powder or a concentrate according to the invention with water, also lie within the scope of the present invention. The said emulsions may be of the water-in-oil or of the oil-in-water type, and may have thick, mayonnaise-like consistency.

It is evident from the foregoing that this invention contemplates compositions containing as little as about 0.5% by weight to as much as about 95% by weight of a compound of Formula I as the active ingredient.

The compositions of the invention may also contain other ingredients, for example, other compounds possessing pesticidal, especially insecticidal, acaricidal, herbicidal or fungicidal properties, as are appropriate to the intended purpose.

Protection of a locus or area from undesirable plants is effected by applying a compound of Formula I, ordinarily in a composition of one of the aforementioned types, to soil in which the seeds of the unwanted plants are present, or to the foliage of the unwanted plants. The active compound, of course, is applied in an amount sufficient to exert the desired action.

The amount of the compound of the invention to be used in combatting undesired plants will naturally depend on the condition of the plants, the degree of activity desired, the formulation used, the mode of application, the climate, the season of the year, and other variables. Recommendations as to precise amounts are, therefore, not possible. In general, however, application to the locus to be protected of from 0.1 to 10.0 kg per hectare of the compound of Formula I will be satisfactory.

EXAMPLES OF ACTIVITY WITH RESPECT TO PLANTS

Primary Tests

In the following examples, the species of plants that were tested were:
Barnyardgrass (watergrass)—*Echinochloa crus-galli*
Large Crabgrass—*Digitaria sanguinalis*
Downy brome—*Bromus tectorum*
Yellow foxtail—*Setaria lutescens*
Redroot pigweed—*Amaranthus retroflexus*
Velvetleaf—*Abutilon theophrasti*
Garden cress—*Lepidium sativum*
Johnson grass—*Sorghum halepense*
Morningglory—*Ipomoea purpurea* L. (Roth)

Test Procedures

The preemergence (soil) herbicidal activity of compounds of Formula I was evaluated by planting seeds of barnyardgrass, garden cress, downy brome, velvetleaf, yellow foxtail, and morningglory in test tubes, nominally measuring 25×200 millimeters, filled about three-quarters full of untreated soil, in each case covered on top with about 2.5 cubic centimeters of soil treated with a certain amount of the test compound. The treated soil applied to the tubes containing the barnyardgrass and cress seeds contained one milligram of the test compound per tube, and contained 0.1 milligram of the test compound per each tube containing the seeds of the other plants. The dosages were approximately 20 and 2.0 pounds of test compound per acre, respectively. The seeds were planted on top of the treated soil and covered with about 1.5 cubic centimeters of untreated soil. The planted soil was held under controlled conditions of temperature, moisture, and light for 9 to 10 days. The amounts of germination and growth in each tube were evaluated on a 0 to 9 scale, the numeric ratings having the following meanings:

| Rating | Meaning |
| --- | --- |
| 9 | No living tissue |
| 8 | Plant severely damaged and expected to die |
| 7 | Plant badly damaged, but expected to live |
| 6 | Moderate damage, but complete recovery expected |
| 5 | Intermediate damage (probably unacceptable for crop plants) |
| 3–4 | Observable damage |
| 1–2 | Plant slightly affected, possibly by the chemical, possibly due to biological variability |
| 0 | No visible effect |

The postemergence (foliar) herbicidal activity of compounds of Formula I was evaluated by spraying 10-day-old large crabgrass plants, 13-day-old pigweed plants, 6-day-old Johnsongrass plants, 9-day-old velvetleaf plants, 9-day-old yellow foxtail plants and 5-day-old morningglory plants to runoff with a liquid formulation of the test compound. The crabgrass and pigweed plants were sprayed with 2.4 millimeters of a 0.25% solution (about ten pounds of the test compound per acre), and other plants were sprayed with 2.4 milliliters of a 0.025% solution (about one pound of the test compound per acre). The sprayed plants were held under controlled conditions of temperature, moisture and light for 7 to 8 days, when the effect of the test compound was evaluated visually, the results being rated on the 0 to 9 scale described above.

All of Compounds Nos. 1 through 15 were tested in both primary test procedures.

Secondary Tests

In the following examples, the species of plants that were tested were:
Barnyardgrass
Downy Brome
Johnsongrass
Wild oats—*Avena fatua*
Yellow foxtail
Goose grass—*Eleusine indica L.*
Yellow nutsedge—*Cyperus esculentus L.*
Cocklebur—*Xanthum pennsylvanicum*
Morningglory
Wild mustard—*Brassica kaber*
Redroot pigweed
Sicklepod—*Cassia obtusifolia*
Velvetleaf
Corn—*Zea mays*
Cotton—*Gossypium hirsutum*
Rice—*Oryza sativa*
Grain sorghum—*Sorghum vulgare*
Soybeans—*Glycine max*
Sugarbeets—*Beta vulgaris*
Wheat—*Triticum aestivum*
Nightshade—*Solanium nigrum* sp.

Test Procedures

The preemergence activity of compounds of Formula I was further determined with respect to certain species of crop plants and common species of weeds, by spraying a formulation of the test compound on soil in small pots in which seeds of the plants had been sown. The postemergence herbicidal activity of compounds of Formula I was evaluated with respect to the crop plants and weeds, by spraying a formulation of the test compound on the foliage of the young growing plants. In each series of tests, the plants were grown in narrow trays and sprayed with the formulation. The results of the tests were evaluated on the basis of the 0-9 scale described with respect to the earlier tests.

Compounds Nos. 1 through 9, 11, 13, and 14 were tested preemergence and Compounds No. 1 through 4, 10, and 13 through 15 were tested post-emergence, in the secondary test procedures.

The spectra and levels of activity in such test procedures of the triazines (of Formula II) which were the respective precursors for the compounds of Formula I that were tested, had already been determined. It was found that each of the compounds of Formula I showed essentailly the spectrum of activity as its precursor, with the level of activity, generally being the same, or slightly lower.

EXAMPLES OF SOLUBILITY

The significantly higher solubility of Compounds of Formula I in common horticultural solvents was demonstrated by determining the approximate solubility of typical individual species of those compounds and their precursor triazines, in xylene at room temperature. The following results were obtained.

TABLE I

| Compound No. | Approximate Solubility at Room Temperature, Grams of Compound per 100 Grams of Xylene |
| --- | --- |
| 1 | 26 |
| 1B (Cyanazine) | 0.3 |
| 5 | >150[a] |
| Atrazine | 0.5 |
| 14 | >150 |
| 14A (Atraton) | 25 |
| 15 | >150 |
| 15A (Ametryne) | >90, <120[b] |

[a] > = greater than
[b] < = less than

We claim:
1. A compound of the formula:

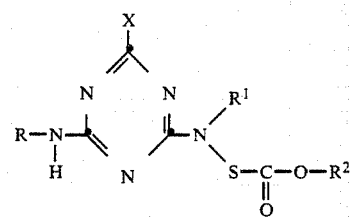

(I)

wherein X is middle halogen, alkoxy or alkylthio of one to three carbon atoms, R is alkyl of two to four carbon atoms, cycloalkyl of three to four carbon atoms, or 1-cyanoalkyl of three to five carbon atoms; $R^1$ is alkyl of one to four carbon atoms or cyclopropyl; $R^2$ is alkyl of from one to eight carbon atoms.

2. A method for controlling unwanted plants at a locus, which comprises applying to the locus an effective amount of a compound of claim 1.

3. A composition adapted to control unwanted plants which comprises an effective amount of a compound of claim 1 and an inert carrier, a surface-active agent, or both.

* * * * *